(12) United States Patent
Garrison

(10) Patent No.: US 8,672,939 B2
(45) Date of Patent: Mar. 18, 2014

(54) SURGICAL DEVICE FOR PERFORMING AN ELECTROSURGICAL PROCEDURE

(75) Inventor: David M. Garrison, Longmont, CO (US)

(73) Assignee: Covidien LP, Mansfield, MA (US)

( * ) Notice: Subject to any disclaimer, the term of this patent is extended or adjusted under 35 U.S.C. 154(b) by 924 days.

(21) Appl. No.: 12/791,112

(22) Filed: Jun. 1, 2010

(65) Prior Publication Data

US 2011/0295251 A1  Dec. 1, 2011

(51) Int. Cl.
*A61B 18/18* (2006.01)

(52) U.S. Cl.
USPC ............................................. 606/52; 606/51

(58) Field of Classification Search
USPC ........................................................ 606/49–52
See application file for complete search history.

(56) References Cited

U.S. PATENT DOCUMENTS

| | | | |
|---|---|---|---|
| D263,020 S | 2/1982 | Rau, III | |
| D295,893 S | 5/1988 | Sharkany et al. | |
| D295,894 S | 5/1988 | Sharkany et al. | |
| D348,930 S | 7/1994 | Olson | |
| 5,578,052 A * | 11/1996 | Koros et al. | 606/174 |
| D384,413 S | 9/1997 | Zlock et al. | |
| D424,694 S | 5/2000 | Tetzlaff et al. | |
| D425,201 S | 5/2000 | Tetzlaff et al. | |
| 6,102,909 A * | 8/2000 | Chen et al. | 606/45 |
| D449,886 S | 10/2001 | Tetzlaff et al. | |
| 6,358,249 B1 * | 3/2002 | Chen et al. | 606/45 |
| 6,361,534 B1 * | 3/2002 | Chen et al. | 606/45 |
| 6,364,879 B1 * | 4/2002 | Chen et al. | 606/45 |
| D457,958 S | 5/2002 | Dycus et al. | |
| D457,959 S | 5/2002 | Tetzlaff et al. | |
| D493,888 S | 8/2004 | Reschke | |
| D496,997 S | 10/2004 | Dycus et al. | |
| D499,181 S | 11/2004 | Dycus et al. | |
| D509,297 S | 9/2005 | Wells | |

(Continued)

FOREIGN PATENT DOCUMENTS

| | | |
|---|---|---|
| DE | 2415263 | 10/1975 |
| DE | 2514501 | 10/1976 |

(Continued)

OTHER PUBLICATIONS

Michael Choti, "Abdominoperineal Resection with the LigaSure Vessel Sealing System and LigaSure Atlas 20 cm Open Instrument" ; Innovations That Work, Jun. 2003.

(Continued)

*Primary Examiner* — Linda Dvorak
*Assistant Examiner* — Jocelyn D Ram

(57) ABSTRACT

An electrosurgical forceps includes a handle and a shaft extending from the handle. The handle is selectively movable to actuate a pair of first and second opposable jaw members pivotably connected to each other at a distal end of the shaft. The jaw members are moveable from an open position to a closed position and are each adapted to connect to an electrosurgical energy source. A first linkage is disposed at least partially within the shaft and is operably coupled between the first jaw member and a second linkage disposed proximal to the first linkage. Selective movement of the handle rotates the second linkage in a first direction, thereby rotating the first linkage in an opposite second direction to move the jaw members between the open and closed positions. In some embodiments, the jaw members are configured in a releasably locked configuration when in the closed position.

11 Claims, 4 Drawing Sheets

(56) References Cited

U.S. PATENT DOCUMENTS

| | | |
|---|---|---|
| D525,361 S | 7/2006 | Hushka |
| D531,311 S | 10/2006 | Guerra et al. |
| D533,942 S | 12/2006 | Kerr et al. |
| 7,150,097 B2 | 12/2006 | Sremicich et al. |
| 7,150,749 B2 | 12/2006 | Dycus et al. |
| D535,027 S | 1/2007 | James et al. |
| 7,156,846 B2 | 1/2007 | Dycus et al. |
| D541,418 S | 4/2007 | Schechter et al. |
| D541,938 S | 5/2007 | Kerr et al |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| 7,597,693 B2 | 10/2009 | Garrison |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| 8,112,871 B2 | 2/2012 | Brandt et al. |
| 8,133,254 B2 | 3/2012 | Dumbauld et al. |
| 8,162,965 B2 | 4/2012 | Reschke et al. |
| 8,187,273 B2 | 5/2012 | Kerr et al. |
| 8,251,994 B2 | 8/2012 | McKenna et al. |
| 8,266,783 B2 | 9/2012 | Brandt et al. |
| 8,277,446 B2 | 10/2012 | Heard |
| 8,287,536 B2 | 10/2012 | Mueller et al. |
| 8,292,067 B2 | 10/2012 | Chowaniec et al. |
| 8,292,886 B2 | 10/2012 | Kerr et al. |
| 8,323,310 B2 | 12/2012 | Kingsley |
| 8,343,150 B2 | 1/2013 | Artale |
| 8,343,151 B2 | 1/2013 | Siebrecht et al. |
| 8,357,159 B2 | 1/2013 | Romero |
| 8,388,647 B2 | 3/2013 | Nau, Jr. et al. |
| 8,409,246 B2 | 4/2013 | Kerr et al. |
| 8,409,247 B2 | 4/2013 | Garrison et al. |
| 8,425,511 B2 | 4/2013 | Olson |
| 8,430,876 B2 | 4/2013 | Kappus et al. |
| 8,430,877 B2 | 4/2013 | Kerr et al. |
| 8,439,911 B2 | 5/2013 | Mueller |
| 8,439,913 B2 | 5/2013 | Horner et al. |
| 8,469,991 B2 | 6/2013 | Kerr |
| 8,469,992 B2 | 6/2013 | Roy et al. |
| 8,480,671 B2 | 7/2013 | Mueller |
| 2005/0090817 A1* | 4/2005 | Phan ............... 606/41 |
| 2005/0187547 A1* | 8/2005 | Sugi ............... 606/48 |
| 2006/0079933 A1* | 4/2006 | Hushka et al. ............... 606/205 |
| 2006/0129146 A1 | 6/2006 | Dycus et al. |
| 2007/0043353 A1 | 2/2007 | Dycus et al. |
| 2007/0078458 A1 | 4/2007 | Dumbauld et al. |
| 2007/0106295 A1 | 5/2007 | Garrison et al. |
| 2007/0142833 A1 | 6/2007 | Dycus et al. |
| 2007/0179499 A1 | 8/2007 | Garrison |
| 2008/0319442 A1 | 12/2008 | Unger et al. |
| 2009/0012520 A1 | 1/2009 | Hixson et al. |
| 2009/0182327 A1 | 7/2009 | Unger |
| 2010/0145334 A1 | 6/2010 | Olson et al. |
| 2010/0280511 A1 | 11/2010 | Rachlin et al. |
| 2011/0034918 A1 | 2/2011 | Reschke |
| 2011/0046623 A1 | 2/2011 | Reschke |
| 2011/0054468 A1 | 3/2011 | Dycus |
| 2011/0054471 A1 | 3/2011 | Gerhardt et al. |
| 2011/0060334 A1 | 3/2011 | Brandt et al. |
| 2011/0060335 A1 | 3/2011 | Harper et al. |
| 2011/0071523 A1 | 3/2011 | Dickhans |
| 2011/0073594 A1 | 3/2011 | Bonn |
| 2011/0077648 A1 | 3/2011 | Lee et al. |
| 2011/0082494 A1 | 4/2011 | Kerr et al. |
| 2011/0118736 A1 | 5/2011 | Harper et al. |
| 2011/0190653 A1 | 8/2011 | Harper et al. |
| 2011/0190765 A1 | 8/2011 | Chojin |
| 2011/0193608 A1 | 8/2011 | Krapohl |
| 2011/0218530 A1 | 9/2011 | Reschke |
| 2011/0230880 A1 | 9/2011 | Chojin et al. |
| 2011/0251605 A1 | 10/2011 | Hoarau et al. |
| 2011/0251606 A1 | 10/2011 | Kerr |
| 2011/0251611 A1 | 10/2011 | Horner et al. |
| 2011/0270245 A1 | 11/2011 | Horner et al. |
| 2011/0270250 A1 | 11/2011 | Horner et al. |
| 2011/0270251 A1 | 11/2011 | Horner et al. |
| 2011/0276048 A1 | 11/2011 | Kerr et al. |
| 2011/0276049 A1 | 11/2011 | Gerhardt |
| 2011/0295251 A1 | 12/2011 | Garrison |
| 2011/0295313 A1 | 12/2011 | Kerr |
| 2011/0301600 A1 | 12/2011 | Garrison et al. |
| 2011/0301602 A1 | 12/2011 | Roy et al. |
| 2011/0301603 A1 | 12/2011 | Kerr et al. |
| 2011/0301604 A1 | 12/2011 | Horner et al. |
| 2011/0301605 A1 | 12/2011 | Horner |
| 2011/0319886 A1 | 12/2011 | Chojin et al. |
| 2011/0319888 A1 | 12/2011 | Mueller et al. |
| 2012/0010614 A1 | 1/2012 | Couture |
| 2012/0083827 A1* | 4/2012 | Artale et al. ............... 606/207 |
| 2012/0303025 A1* | 11/2012 | Garrison ............... 606/51 |

FOREIGN PATENT DOCUMENTS

| | | |
|---|---|---|
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 10 2004 026179 | 12/2005 |
| DE | 20 2007 009317 | 10/2007 |
| DE | 19738457 | 1/2009 |
| EP | 1159926 | 12/2001 |
| EP | 1 486 177 A2 | 12/2004 |
| EP | 1 530 952 A1 | 5/2005 |
| EP | 1 642 543 A1 | 4/2006 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11-070124 | 5/1998 |
| JP | 2000-102545 | 9/1998 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |
| WO | WO 00/36986 | 6/2000 |
| WO | WO 01/54604 | 8/2001 |
| WO | WO 2005/004734 A1 | 1/2005 |
| WO | WO 2005/004735 A1 | 1/2005 |
| WO | WO 2005/110264 | 11/2005 |

OTHER PUBLICATIONS

Chung et al., "Clinical Experience of Sutureless Closed Hemorrhoidectomy with LigaSure" Diseases of the Colon & Rectum vol. 46, No. 1 Jan. 2003.

Tinkcler L.F., "Combined Diathermy and Suction Forceps" , Feb. 6, 1967 (Feb. 6, 1965), British Medical Journal Feb. 6, 1976, Vol. 1, nr. 5431 p. 361, ISSN: 0007-1447.

Carbonell et al., "Comparison of the Gyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.

(56) References Cited

OTHER PUBLICATIONS

Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.

Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.

(56) References Cited

OTHER PUBLICATIONS

Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18676 dated Sep. 19, 2003.
Int'l Search Report PCT/US03/28534 dated Dec. 19, 2003.
Int'l Search Report PCT/USO4/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
U.S. Appl. No. 09/387,883, filed Sep. 1, 1999, Schmaltz.
U.S. Appl. No. 09/591,328, filed Jun. 9, 2000, Ryan.
U.S. Appl. No. 12/336,970, filed Dec. 17, 2008, Sremcich.

* cited by examiner

SURGICAL DEVICE FOR PERFORMING AN ELECTROSURGICAL PROCEDURE

BACKGROUND

1. Technical Field

The following disclosure relates to an apparatus, system, and method for performing an electrosurgical procedure and, more particularly, to an apparatus, system and method that utilizes energy to seal and/or divide tissue.

2. Description of Related Art

Electrosurgical apparatuses (e.g., electrosurgical forceps) are well known in the medical arts and typically include a handle, a shaft, and an end effector assembly operatively coupled to a distal end of the shaft that is configured to manipulate tissue (e.g., grasp and seal tissue). Electrosurgical forceps utilize both mechanical clamping action and electrical energy to effect hemostasis by heating the tissue and blood vessels to coagulate, cauterize, seal, cut, desiccate, and/or fulgurate tissue As an alternative to open electrosurgical forceps for use with open surgical procedures, many modern surgeons use endoscopes and endoscopic electrosurgical apparatus (e.g., endoscopic forceps) or laparoscopic forceps for remotely accessing organs through smaller, puncture-like incisions. As a direct result thereof, patients tend to benefit from less scarring, fewer infections, shorter hospital stays, less pain, less restriction of activity, and reduced healing time. Typically, the forceps are inserted into the patient through one or more various types of cannulas or access ports (typically having an opening that ranges from about five millimeters to about twelve millimeters) that has been made with a trocar. As such, smaller cannulas are typically more desirable relative to larger cannulas. Forceps that are configured for use with small cannulas (e.g., cannulas less than five millimeters) may present design challenges for a manufacturer of electrosurgical instruments.

SUMMARY

According to an embodiment of the present disclosure, an electrosurgical forceps includes a handle and a shaft extending from the handle. The handle is selectively movable to actuate a pair of first and second opposable jaw members pivotably connected to each other at a distal end of the shaft. The jaw members are moveable from an open position to a closed position and are each adapted to connect to an electrosurgical energy source. A first linkage is disposed at least partially within the shaft and is operably coupled between the first jaw member and a second linkage disposed proximal to the first linkage. Selective movement of the handle rotates the second linkage in a first direction, thereby rotating the first linkage in an opposite second direction to move the jaw members between the open and closed positions.

According to another embodiment of the present disclosure, an electrosurgical forceps includes a handle having a shaft extending therefrom and selectively movable to actuate a pair of first and second opposable jaw members pivotably connected to each other at a distal end of the shaft. The jaw members are moveable from an open position, wherein the jaw members are in spaced relation relative to one another, to a closed position wherein the jaw members cooperate to grasp tissue therebetween. Each of the jaw members are adapted to connect to an electrosurgical energy source to conduct energy through tissue grasped therebetween to effect a tissue seal. The forceps also includes a 2-pin linkage disposed at least partially within the shaft and operably coupled between the first jaw member and an 3-pin linkage disposed proximal to the 2-pin linkage. The 3-pin linkage is operably coupled at a first end to a distal end of a drive element. The drive element is operably coupled at a proximal end to the handle such that selective movement of the handle causes movement of the drive element relative to the shaft to rotate the 3-pin linkage in a first direction, thereby rotating the 2-pin linkage in an opposite second direction. The coupling between the 2-pin linkage and the 3-pin linkage is movable between a first position to move the jaw members to the open position, and a second position to move the jaw members to the closed position in a releasably locked configuration.

According to another embodiment of the present disclosure, a method of performing an electrosurgical procedure includes the step of providing an electrosurgical forceps. The electrosurgical forceps includes a handle having a shaft extending therefrom and selectively movable to actuate a pair of first and second opposable jaw members pivotably connected to each other at a distal end of the shaft. The jaw members are moveable from an open position, wherein the jaw members are in spaced relation relative to one another, to a closed position wherein the jaw members cooperate to grasp tissue therebetween. Each of the jaw members are adapted to connect to an electrosurgical energy source to conduct energy through tissue grasped therebetween to effect a tissue seal. The forceps also includes a first linkage disposed at least partially within the shaft and operably coupled between the first jaw member and a second linkage disposed proximal to the first linkage. The method also includes the step of selectively moving the handle to rotate the second linkage in a first direction, thereby rotating the first linkage in an opposite second direction to move the jaw members between the open and closed positions. The method also includes the steps of actuating the jaw members to grasp tissue therebetween and delivering electrosurgical energy from the electrosurgical energy source to each of the jaw members to effect a tissue seal.

BRIEF DESCRIPTION OF THE DRAWINGS

Various embodiments of the present disclosure are described hereinbelow with references to the drawings, wherein.

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

As noted above, it may prove useful in the arts to provide an electrosurgical apparatus that is suitable for use during catheter-based endoluminal procedures and/or for use with various access ports, including but not limited to those that are greater than and/or less than five millimeters. The present disclosure may be particularly advantageous for use with flexible-shafted instrument designs, such as catheter-based designs used in endoluminal procedures. With this purpose in mind, the present disclosure includes an electrosurgical forceps that includes a pair of jaw members associated with an end effector assembly of the electrosurgical forceps. The pair of jaw members are operably coupled to an electrosurgical energy source and are each configured to conduct an electrical potential (e.g., positive or negative) therethrough that is opposite to that of the other electrode (e.g., in a bipolar configuration). In some embodiments, a drive element mechanically cooperates with a handle assembly and a releasably locking linkage assembly to move the jaw members from an open configuration to a closed configuration. In the closed configuration, the jaw members are releasably locked relative to one another and form a closed loop electrical circuit such that a desired tissue effect (e.g., tissue seal) may be achieved.

Figure 1:
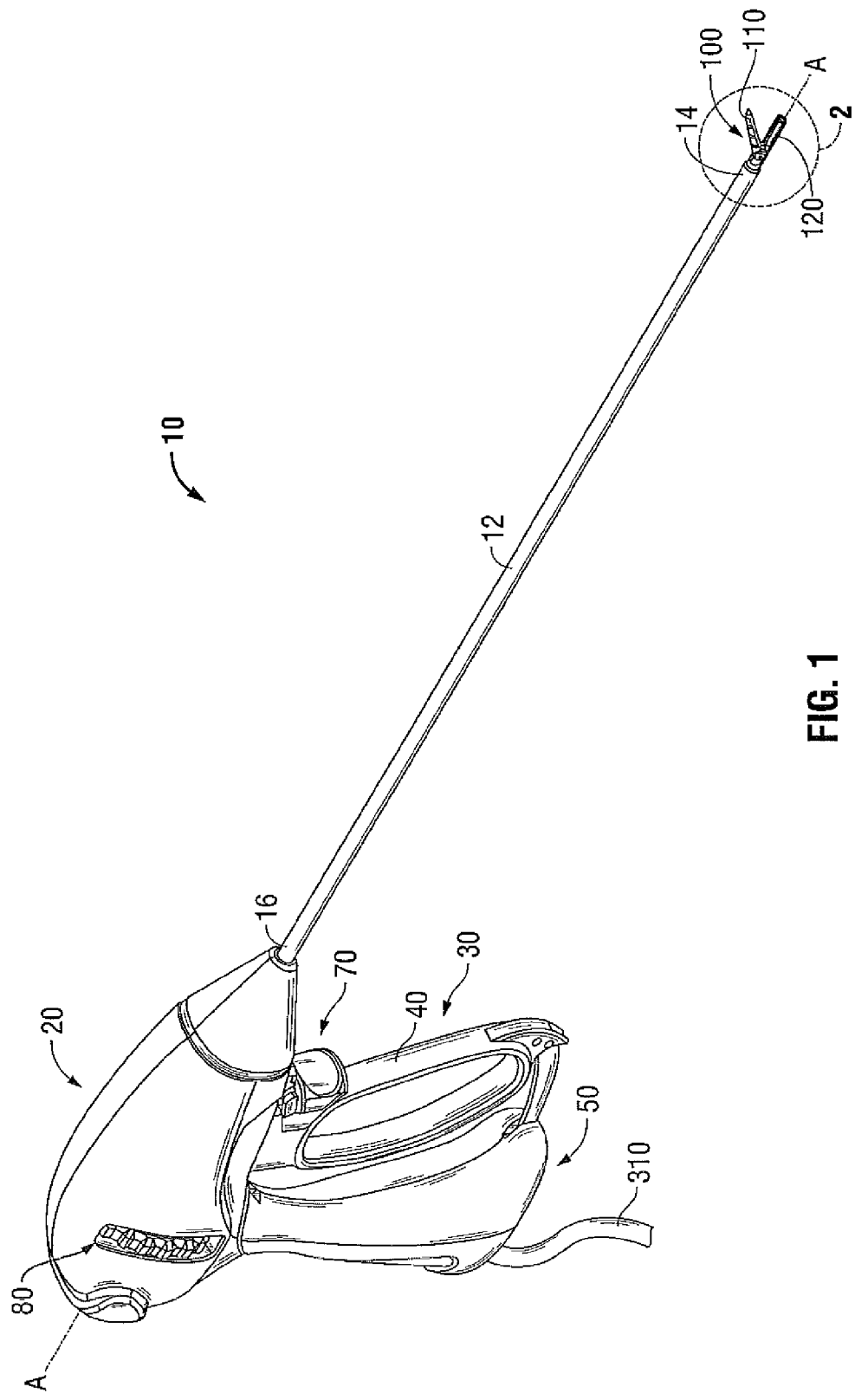
FIG. 1 is a perspective view of an endoscopic bipolar forceps showing a housing, a shaft, and an end effector assembly in accordance with an embodiment of the present disclosure.

Turning now to FIG. 1, an embodiment of an endoscopic bipolar forceps 10 is shown for use with various surgical procedures and generally includes a housing 20, a handle assembly 30, a rotating assembly 80, a trigger assembly 70, and an end effector assembly 100 that mutually cooperate to grasp, seal, and divide tubular vessels and vascular tissue. Although the majority of the figure drawings depict a bipolar forceps 10 for use in connection with endoscopic surgical procedures, the present disclosure may be used for more traditional open surgical procedures. For the purposes herein, the forceps 10 is described in terms of an endoscopic instrument, however, it is contemplated that an open version of the forceps may also include the same or similar operating components and features as described below.

In the drawings and in the descriptions that follow, the term "proximal", as is traditional, will refer to the end of the forceps 10 that is closer to the user, while the term "distal" will refer to the end that is farther from the user.

Forceps 10 includes a shaft 12 that has a distal end 14 dimensioned to mechanically engage the end effector assembly 100 and a proximal end 16 that mechanically engages the housing 20. Proximal end 16 of shaft 12 is received within housing 20 and appropriate mechanical and electrical connections relating thereto are established.

Forceps 10 includes an electrosurgical cable 310 that connects the forceps 10 to a source of electrosurgical energy, e.g., a generator (not shown). One such source of electrosurgical energy is described in commonly-owned U.S. Pat. No. 6,033, 399 entitled "ELECTROSURGICAL GENERATOR WITH ADAPTIVE POWER CONTROL". Cable 310 is internally divided into several cable leads (not shown) that each transmit electrical potentials through their respective feed paths through the forceps 10 to the end effector assembly 100.

For a more detailed description of handle assembly 30, movable handle 40, rotating assembly 80, and electrosurgical cable 310 (including line-feed configurations and/or connections) reference is made to commonly owned Patent Publication No. 2003/0229344, filed on Feb. 20, 2003, entitled VESSEL SEALER AND DIVIDER AND METHOD OF MANUFACTURING THE SAME.

Handle assembly 30 includes a fixed handle 50 and a movable handle 40. Fixed handle 50 is integrally associated with housing 20 and handle 40 is movable relative to fixed handle 50 as explained in more detail below with respect to the operation of the forceps 10. Rotating assembly 80 is operatively connected to the housing 20 and is rotatable approximately 180 degrees in either direction about a longitudinal axis "A-A" (See FIG. 1).

As mentioned above, end effector assembly 100 is attached at the distal end 14 of shaft 12 and includes a pair of opposing jaw members 110 and 120. Movable handle 40 of handle assembly 30 is operatively connected to a drive element (not shown) that, together, mechanically cooperate to impart movement of the jaw members 110 and 120 from an open position wherein the jaw members 110 and 120 are disposed in spaced relation relative to one another, to a clamping or closed position wherein the jaw members 110 and 120 cooperate to grasp tissue therebetween. With this purpose in mind, forceps 10 may include any suitable number of configurations, components, mechanical connections, and/or components (e.g., gears, links, springs, rods, etc.), and/or electromechanical connections, configurations, and/or components such that forceps 10 may function as intended.

In some embodiments, forceps 10 may be configured such that it is re-usable or such that it is fully or partially disposable depending upon a particular purpose or to achieve a particular result. For example, end effector assembly 100 may be selectively and releasably engageable with distal end 14 of the shaft 12 and/or the proximal end 16 of shaft 12 may be selectively and releasably engageable with the housing 20 and the handle assembly 30. In either of these two instances, the forceps 10 would be considered "partially disposable" or "reposable", e.g., a new or different end effector assembly 100 (or end effector assembly 100 and shaft 12) selectively replaces the old end effector assembly 100 as needed. In some embodiments, the presently disclosed electrical connections would have to be altered to modify the instrument to a reposable forceps.

Figure 2:
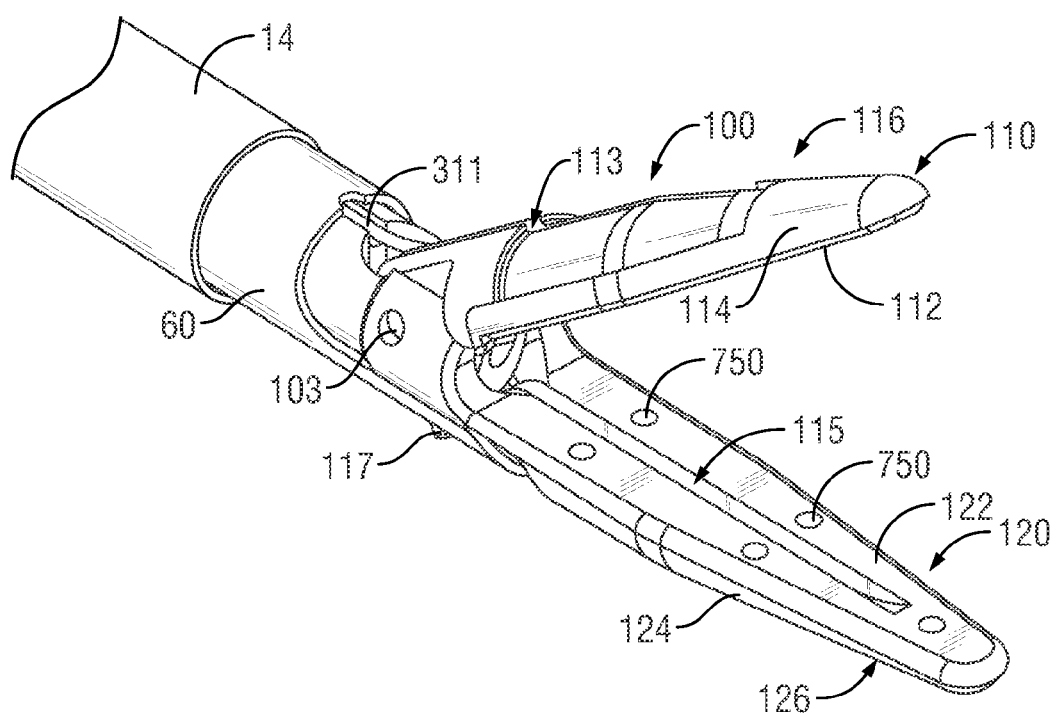
FIG. 2 is an enlarged, left perspective view of the end effector assembly of FIG. 1 with the jaw members in open configuration.

As shown best in FIG. 2, the end effector assembly 100 includes opposing jaw members 110 and 120 that cooperate to effectively grasp tissue for sealing purposes. The end effector assembly 100 may be designed as a unilateral assembly (See FIGS. 3A and 3B), i.e., jaw member 120 is fixed relative to the shaft 12 and jaw member 110 pivots about a pivot pin 103 relative to jaw member 120 to grasp tissue, or as a bilateral assembly, i.e., jaw members 110 and 120 pivot about pivot pin 103 relative to each other to grasp tissue. In some embodiments and as will be discussed in further detail below, jaw members 110, 120 are operably coupled to each other via pivot pin 103 about which pivoting jaw member 110 pivots relative to stationary jaw member 120.

In the illustrated embodiment, the unilateral end effector assembly 100 includes one stationary or fixed jaw member 120 mounted in fixed relation to the shaft 12 and a pivoting jaw member 110 mounted about a pivot pin 103 attached to the stationary jaw member 120. A reciprocating sleeve 60 is slidingly disposed within the shaft 12 and is remotely operable by a drive element. The pivoting jaw member 110 includes a detent or protrusion 117 that extends from jaw member 110 through an aperture (not shown) disposed within the reciprocating sleeve 60. Pivoting jaw member 110 is actuated by sliding the sleeve 60 axially within shaft 12 such that a distal end of the aperture abuts against detent 117 on pivoting jaw member 110. Pulling sleeve 60 proximally closes jaw members 110 and 120 about tissue and the like, and pushing sleeve 60 distally opens jaw members 110 and 120.

As illustrated in FIG. 2, a knife channel 115 runs through the center of jaw member 120 (a complementary knife channel may be formed in jaw member 110) such that a blade from a knife assembly (not shown) may cut through the tissue grasped between jaw members 110 and 120 when jaw members 110 and 120 are in a closed position. Details relating to the knife channel 115 and a knife actuation assembly including trigger assembly 70 are explained in limited detail herein and explained in more detail with respect to commonly-owned U.S. Pat. Nos. 7,156,846 and 7,150,749 to Dycus et al.

As best shown in FIG. 2, jaw member 110 also includes a jaw housing 116 that has an insulative substrate or insulator 114 and an electrically conducive surface 112. Insulator 114 is configured to secure the electrically conductive sealing surface 112 to the jaw housing 116. This may be accomplished by overmolding insulator 114 about jaw housing 116. Moveable jaw member 110 also includes a wire channel 113 configured to guide a cable lead 311 into electrical continuity with electrically conductive sealing surface 112, as described in more detail below.

Jaw member 120 includes similar elements to jaw member 110 such as jaw housing 126 having an insulator 124 and an electrically conductive sealing surface 122 that is secured to the jaw housing 126 by the insulator 124. This may be accomplished, for example, by overmolding insulator 124 about jaw housing 126.

All of these manufacturing techniques produce jaw members 110, 120 having an electrically conductive surface 112, 122, respectively, that is substantially surrounded by an insulating substrate 114, 124 (See FIG. 2). The illustrated embodiment of FIG. 2 is illustrative only in that either one of or both of jaw members 110 or 120 may be configured to be devoid of an insulating substrate 114 or 124. For example, in some embodiments, jaw member 110 may include insulating substrate 114 and jaw member 120 may be configured such that insulating substrate 124 is removed and/or end effector assembly 100 may be manufactured such that jaw member 120 does not include an insulating substrate. The insulators 114, 124, electrically conductive sealing surfaces 112, 122, and the jaw housings 116, 126 are configured to limit and/or reduce many of the known undesirable effects related to tissue sealing, e.g., flashover, thermal spread and stray current dissipation. In other embodiments, the jaw members 110 and 120 may be manufactured from a ceramic-like material and the electrically conductive surfaces 112 and 122 are coated onto the ceramic-like jaw members 110 and 120, respectively.

As best shown in FIG. 2, jaw member 120 may include a series of stop members 750 disposed on the inner facing surfaces of the electrically conductive sealing surface 122 to facilitate gripping and manipulation of tissue and to define a gap between opposing jaw members 110 and 120 during sealing and cutting of tissue. The series of stop members 750 may be employed on one or both jaw members 110 and 120 depending upon a particular purpose or to achieve a desired result. A detailed discussion of stop members 750 as well as various manufacturing and assembling processes for attaching and/or affixing the stop members 750 to the electrically conductive sealing surfaces 112, 122 are described in commonly owned U.S. Pat. No. 7,473,253 to Dycus et al.

Figure 3A:
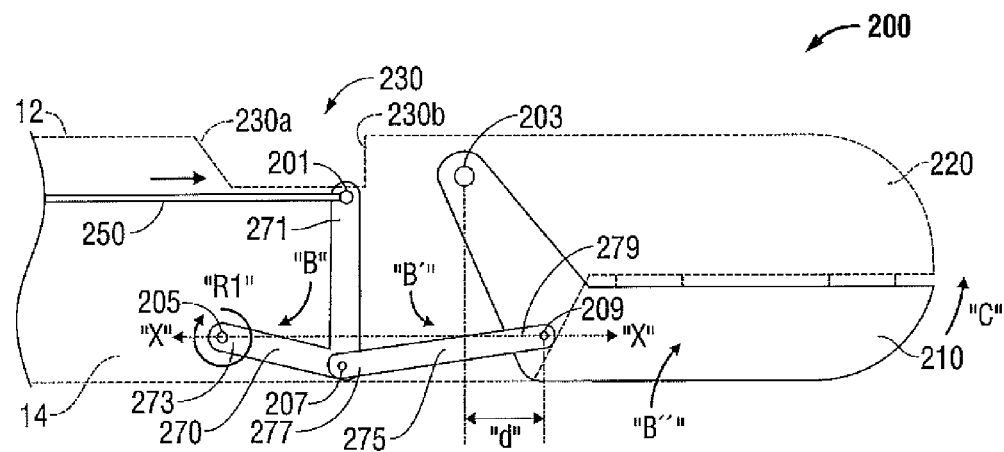
FIG. 3A is a schematic, side elevational view of an end effector assembly according to one embodiment of the present disclosure, with the jaw members in a closed configuration.
Figure 3B:
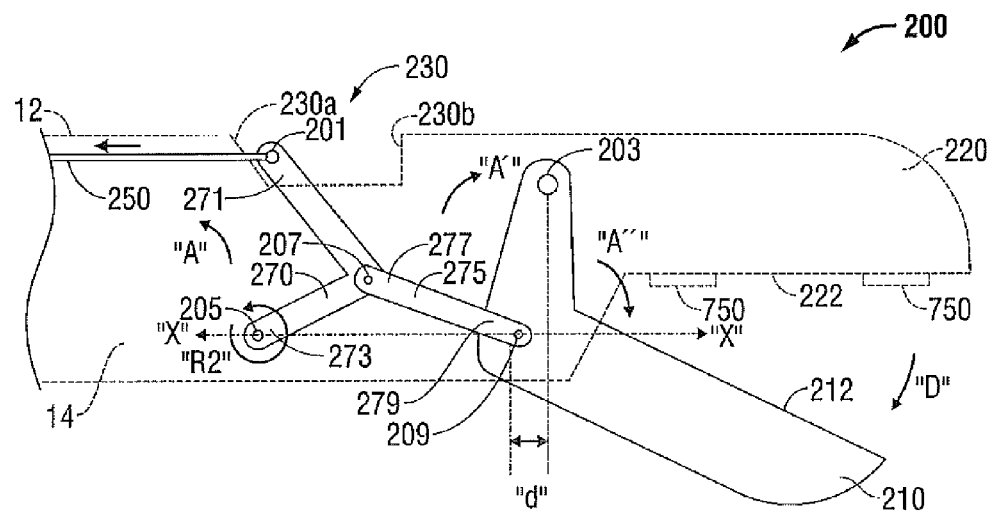
FIG. 3B is a schematic, side elevational view of the end effector assembly of FIG. 3A, with the jaw members in an open configuration.

Turning now to FIGS. 3A and 3B, another embodiment of forceps 10 including an end effector assembly 200, in accordance with the present disclosure, is shown and described. End effector assembly 200 may include some, if not all, of the features and elements associated with end effector assembly 100 and as described above with reference to FIGS. 1 and 2. While end effector assembly 200 is shown as having a unilateral jaw member arrangement, end effector assembly 200 may, in certain embodiments, have a bilateral jaw member arrangement.

As shown in FIGS. 3A and 3B, end effector assembly 200 includes a pair of opposing jaw members 210 and 220 having electrically conductive tissue sealing surfaces 212 and 222, respectively. More specifically, end effector assembly 200 includes a movable jaw member 210 that pivots about a pivot pin 203 relative to a stationary jaw member 220 that is monolithically formed with the distal end 14 of shaft 12 to grasp tissue. Movable handle 40 of handle assembly 30 is operatively coupled to a proximal end (not shown) of a drive element 250 (e.g., rod, shaft, cable, etc.) that, together, mechanically cooperate to impart movement of jaw member 210 relative to stationary jaw member 220 from an open position (see FIG. 3B), wherein the jaw members 210 and 220 are disposed in spaced relation relative to one another, to a clamping or closed position (see FIG. 3A), wherein jaw members 210 and 220 cooperate to grasp tissue therebetween.

With this purpose in mind, end effector assembly 200 employs a releasably locking linkage assembly including a 3-pin linkage 270 operably coupled at a first end 271 to the drive element 250 via a pivot pin 201 and at a second end 273 to a pivot pin 205 affixed to the structure of shaft 12 by any suitable method (not explicitly shown). In this manner, linkage 270 pivots about pivot pin 205 while pivot pin 205 remains stationary relative to shaft 12. Between the first and second ends 271, 273, linkage 270 is operably coupled via a pivot pin 207 to a first end 277 of a 2-pin linkage 275. A second end 279 of 2-pin linkage 275 is, in turn, operably coupled to jaw member 210 via a pivot pin 209. In some embodiments, linkage 270 may be generally L-shaped.

In order to open end effector assembly 200, drive element 250 is withdrawn or pulled in a proximal direction (see FIG. 3B), by actuating movable handle 40 relative to fixed handle 50. In order to close end effector assembly 200, drive element 250 is pushed or moved in a distal direction (see FIG. 3A), by actuating movable handle 40 relative to fixed handle 50. By way of example, moving drive element 250 in the proximal direction, as depicted in FIG. 3B, may be effected by squeezing movable handle 40 toward stationary handle 50. In this scenario, moving drive element 250 in the distal direction, as depicted in FIG. 3A, may be effected by approximating movable handle 40 away from stationary handle 50. In some embodiments, the configuration described in the above scenario may be reversed, e.g., squeezing movable handle 40 will move drive element 250 in the distal direction and approximating movable handle 40 away from stationary handle 50 will move drive element 250 in the proximal direction.

An aperture 230 is defined through the shaft 12 and has a proximal stop 230a and a distal stop 230b configured to limit the movement of movable jaw member 210 between the open and closed configurations, as described in greater detail below. Proximal and distal stops 230a and 230b may be disposed along any suitable location of shaft 12 to achieve various desired effects.

In operation, when the drive element 250 is pulled in the proximal direction to effect opening of the end effector assembly 200, as depicted in FIG. 3B by arrow "D", the second end 273 of linkage 270 rotates about pivot pin 205 (e.g., in a counter clock-wise direction), as depicted by rotational arrow "R2", such that the first end 271 of linkage 270 rotates within aperture 230 toward proximal stop 230a. Rotation of the second end 273 of linkage 270 about pivot pin 205 in the "R2" direction, in turn, causes linkages 270 and 275 to rotate relative to each other about pivot pin 207 in opposing directions (e.g., counter clock-wise and clock-wise). More specifically and with reference to FIG. 3B, linkage 270 rotates about pivot pin 207 in the direction depicted by rotational arrow "A" and linkage 275 rotates about pivot pin 207 in the direction depicted by rotational arrow "A" and about pivot pin 209 in the direction depicted by rotational arrow "A". The respective rotational movements of linkages 270 and 275 at pivot pins 207 and 209 operates to rotate jaw member 210 about pivot pin 203 into the open position relative to jaw member 220, as depicted by rotational arrow "A" in FIG. 3B. As linkage 270 rotates about pivot pin 205 in the "R2" direction, movement of the first end 271 of linkage 270 within aperture 230 and, thus, rotation of linkage 270 about pivot pin in the "R2" direction, is limited by the proximal stop 230a to dictate the maximum distance between jaw members 220 and 210 when end effector assembly 200 is in the open position. That is, the first end 271 of linkage 270 may abut proximal stop 230a upon rotation of linkage 270 about pivot pin 205 in the "R2" direction to prevent further rotation of jaw member 210 about pivot pin 203 in the "A" direction.

When the drive element 250 is pushed in the distal direction to effect closing of the end effector assembly 200, as depicted in FIG. 3A, the second end 273 of linkage 270 rotates about pivot pin 205 (e.g., in the clock-wise direction), as depicted by rotational arrow "R1", such that the first end 271 of linkage 270 rotates within aperture 230 toward distal stop 230b. Rotation of the second end 273 of linkage 270 about pivot pin 205 in the "R1" direction, in turn, causes linkages 270 and 275 to rotate relative to each other about pivot pin 207 in opposing directions (e.g., counter clock-wise and clock-wise). More specifically and with reference to FIG. 3A, linkage 270 rotates about pivot pin 207 in the direction depicted by rotational arrow "B" and linkage 275 rotates about pivot pin 207 in the direction depicted by rotational arrow "W" and about pivot pin 209 in the direction depicted by rotational arrow "B". The respective rotational movements of linkages 275 and 270 at pivot pins 209 and 207 operate to rotate jaw member 210 about pivot pin 203 into the closed position relative to jaw member 220, as depicted by rotational arrow "C" in FIG. 3A. As linkage 270 rotates about pivot pin 205 in the "R1" direction, movement of the first end 271 of linkage 270 within aperture 230 and, thus, rotation of linkage 270 about pivot pin in the "R1" direction, is limited by the distal stop 230b. That is, the first end 271 of linkage 270 may abut distal stop 230b upon rotation of linkage 270 about pivot pin 205 in the "R1" direction to prevent further rotation of jaw member 210 about pivot pin 203 in the "C" direction. In this manner, jaw member 210 may be prevented from rotating too far in the "C" direction and, thereby applying too great a pressure or closing force on tissue disposed between the jaw members 210, 220.

As shown in FIGS. 3A and 3B, a longitudinal axis "X-X" is defined through pivot pin 205 and pivot pin 209 such that pivot pins 205 and 209 are collinear on longitudinal axis "X-X". Upon movement of the end effector assembly 200 into the open position, as shown in FIG. 3B, pivot pin 207 is disposed "above" longitudinal axis "X-X". That is, pivot pin 207 is disposed between longitudinal axis "X-X" and the surface of shaft 12 through which aperture 230 is defined. Conversely, upon movement of the end effector assembly 200 into the closed position, as shown in FIG. 3A, pivot pin 207 is disposed "below" longitudinal axis "X-X". That is, pivot pin 207 is disposed on the opposite side of longitudinal axis "X-X" than as described above with respect to the open position of end effector assembly 200. When disposed "below" longitudinal axis "X-X", pivot pin 207 is disposed in a so-called "over-the-center" position such that when end effector assembly 200 is in the closed position, jaw member 210 is releasably locked in the closed position relative to jaw member 220. In this configuration, the only force (assuming only forces less than the structural strength of the components of end effector assembly 200) that will break or unlock the "over-the-center" locked configuration of end effector assembly 200 is the proximal pulling of drive element 250 to urge the connection between linkages 270, 275 at pivot pin 207 in the "A" direction such that pivot pin 207 is disposed "above" longitudinal axis "X-X", thereby allowing jaw members 210, 220 to be moved to the open configuration, as shown in FIG. 3B. When pivot pin 207 is collinear with pivot pins 205 and 209 on longitudinal axis "X-X", linkages 270 and 275 are in a state of unstable equilibrium relative each other.

Distal stop 230b prevents the pivot pin 207 from rotating too far "over-the-center". More specifically, as jaw members 210, 220 are moved to the closed position such that jaw member 210 engages jaw member 220, a maximum force between jaw members 210, 220 occurs when pins 205, 207, and 209 are collinear on axis "X-X". As pin 207 moves from being collinear with pins 205 and 209 on axis "X-X" to "below" axis "X-X", the force between jaw members 210, 220 decreases and the first end 271 of linkage 270 rotates within aperture 230 to abut distal stop 230b such that pin 207 is now disposed in the "over-the-center" position and jaw members 210, 220 are releasably locked in the closed position with a desired force therebetween. In this manner, the abutment of the first end 271 of linkage 280 against distal stop 230b operates to limit the distance that pin 207 may travel "below" axis "X-X". As discussed in detail below, jaw members 210, 220 may be configured to engage initially at respective distal ends thereof and subsequently flex toward one another to facilitate movement of pin 207 "over-center".

As shown in the illustrated embodiment of FIGS. 3A and 3B, pivot pins 203 and 209 are separated by a horizontal distance "d". As the distance "d" between pivot pins 203 and 209 is increased or decreased, the opening and closing relationship between jaw members 210, 220 is altered. More specifically, increasing the distance "d" between pivot pins 203 and 209 by moving the location of pivot pin 203 proximally along jaw member 220, results in a greater opening distance between respective distal ends of jaws 210, 220 for a given angle of rotation "A". Likewise, decreasing the distance "d" between pivot pins 203 and 209 by moving the location of pivot pin 203 distally along jaw member 220, results in a lesser opening distance between respective distal ends of jaws 210, 220 for a given angle of rotation "A". In this way, distance "d" may be adjusted to achieve the desired combination of effective jaw member length, opening angle, and mechanical advantage.

Since the force between jaw members 210, 220 is at a maximum when pins 205, 207, 209 are collinear on axis "X-X", a compliance mechanism may be employed to facilitate movement of pin 207 "over-center". For example, jaw members 210, 220 may be configured to engage initially at respective distal ends thereof and subsequently flex toward one another proximal of the distal ends to facilitate movement of pin 207 "over-center". Alternatively or additionally, linkages 270 and/or 275 may be at least semi-flexible such that when pins 205, 207, 209 are collinear on axis "X-X", linkages 270 and/or 275 may compress to facilitate movement of pin 207 "over-center". In either scenario, a stable "over-the-center" latching mechanism is created to facilitate the locking and unlocking of jaw members 210, 220.

In the manner described in the above scenarios, distance "d" may be altered to affect the opening and closing relationship between jaw members 210, 220. For example, jaw member 210 may be configured to close such that jaw members 210 and 220 are either substantially parallel or substantially non-parallel (e.g., over-parallel) relative to one another when end effector assembly 200 is in the closed position. In certain scenarios, end effector assembly 200 may be configured such that a distal end portion of jaw member 210 engages jaw member 220, a stop member 750 (e.g., disposed on either inner facing surface of jaw member 210, 220), and/or tissue disposed between jaw members 210, 220 prior to a proximal end portion of jaw member 210. In other scenarios, end effector assembly 200 may be oppositely configured such that the proximal and distal end portions of jaw member 210 are reversed in the above described scenario.

Figure 4:
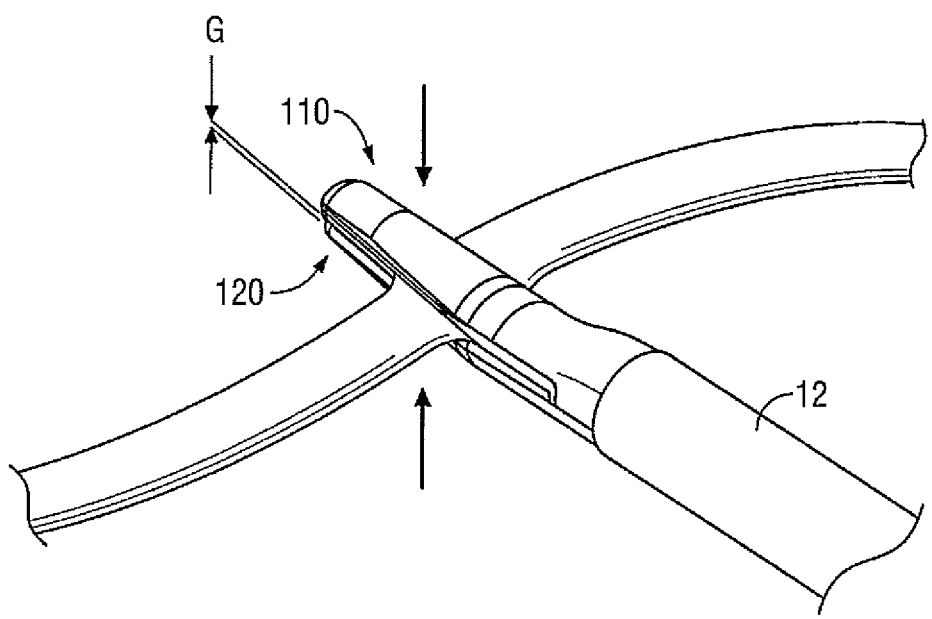
FIG. 4 is an enlarged, rear, perspective view of the end effectors shown grasping tissue.

FIG. 4 shows forceps 10 grasping tissue. While for purposes of discussion the forceps 10 shown in FIG. 4 is described below with reference to the embodiment of FIGS. 1 and 2, the description below may also apply to the embodiment of FIGS. 3A and 3B. As the handle 40 is squeezed, jaw member 110 is approximated toward jaw member 120 to a clamped or closed position about tissue. Once jaws members 110 and 120 are fully compressed about the tissue, forceps 10 is now ready for selective application of electrosurgical energy and subsequent separation of the tissue. By controlling the intensity, frequency, and duration of the electrosurgical energy applied to tissue, the operator can either cauterize, coagulate/desiccate, seal, cut, and/or simply reduce or slow bleeding. Two mechanical factors play an important role in determining the resulting thickness of the sealed tissue and effectiveness of the seal, i.e., the pressure applied between opposing jaw members 110 and 120 and the gap distance "G" between the opposing sealing surfaces 112, 122 of the jaw members 110 and 120 during the sealing process.

As mentioned above, at least one jaw member (e.g., jaw member 120, jaw member 220) may include a stop member 750 that limits the movement of opposing jaw members 110, 120 (or jaw members 210, 220) relative to one another. The stop member 750 extends from the sealing surface 122 (or sealing surface 222) a predetermined distance according to the specific material properties (e.g., compressive strength, thermal expansion, etc.) to yield a consistent and accurate gap distance "G" during sealing (FIG. 4). In some embodiments, the gap distance between opposing sealing surfaces 112 and 122 (or 212 and 222) during sealing ranges from about 0.001 inches to about 0.006 inches and, in other embodiments, between about 0.002 and about 0.003 inches. The non-conductive stop members 750 may be, without limitation, molded onto the jaw members 110 and 120 (or jaw members 210 and 220) via overmolding, injection molding, etc., stamped onto the jaw members 110, 120 (or jaw members 210, 220), or deposited (e.g., deposition) onto the jaw members 110 and 120 (or jaw members 210, 220). For example, one technique involves thermally spraying a ceramic material onto the surface of the jaw member to form the stop members 750. Several suitable thermal spraying techniques may be utilized including, for example, depositing a broad range of heat resistant and insulative materials on various surfaces to create stop members 750 for controlling the gap distance between electrically conductive surfaces 112 and 122 (or sealing surfaces 212 and 222).

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical forceps, comprising:
a handle having a shaft extending therefrom and selectively movable to actuate a pair of first and second opposable jaw members pivotably connected to each other at a distal end of the shaft, the jaw members moveable from an open position, wherein the jaw members are in spaced relation relative to one another, to a closed position wherein the jaw members cooperate to grasp tissue therebetween, each of the jaw members adapted to connect to an electrosurgical energy source to conduct energy through tissue grasped therebetween to effect a tissue seal; and
a 2-pin linkage disposed at least partially within the shaft and operably coupled between the first jaw member and a 3-pin linkage disposed proximal to the 2-pin linkage, the 3-pin linkage being operably coupled at a first end to a distal end of a drive element, the drive element operably coupled at a proximal end to the handle such that selective movement of the handle causes movement of the drive element relative to the shaft to rotate the 3-pin linkage in a first direction, thereby rotating the 2-pin linkage in an opposite second direction, wherein the coupling between the 2-pin linkage and the 3-pin linkage is movable between a first position to move the jaw members to the open position, and a second position to move the jaw members to the closed position in a releasably locked configuration.

2. An electrosurgical forceps according to claim 1, wherein the first end of the 3-pin linkage is configured to move within an aperture defined through the shaft upon selective movement of the handle, the aperture including a distal stop configured to limit rotational movement of the 3-pin bracket in a first direction and a proximal stop to limit rotational movement of the 3-pin linkage in a second direction.

3. An electrosurgical forceps according to claim 1, wherein the coupling between the 2-pin linkage and the first jaw member is collinear with the second end of the 3-pin linkage along a longitudinal axis, wherein the first and second positions of the coupling between the 2-pin linkage and the 3-pin linkage correspond to opposite sides of the longitudinal axis.

4. An electrosurgical forceps according to claim 3, wherein the coupling between the 2-pin linkage and the 3-pin linkage is movable to a third position collinear with the longitudinal axis such that the 2-pin and 3-pin linkages are in a state of unequal equilibrium relative to each other.

5. An electrosurgical forceps according to claim 1, wherein the 2-pin linkage is operably coupled to the 3-pin linkage via a first pivot pin and to the first jaw member via a second pivot pin.

6. An electrosurgical forceps according to claim 1, wherein the 3-pin linkage rotates in a counter clock-wise direction to move the jaw members to the open position and in a clockwise direction to move the jaw members to the closed position.

7. An electrosurgical forceps according to claim 1, wherein the 2-pin linkage is substantially linear and the 3-pin linkage is generally L-shaped.

8. An electrosurgical forceps, comprising:
a handle having a shaft extending therefrom and selectively movable to actuate a pair of first and second opposable jaw members pivotably connected to each other at a distal end of the shaft, the jaw members moveable from an open position, wherein the jaw members are in spaced relation relative to one another, to a closed position wherein the jaw members cooperate to grasp tissue therebetween, each of the jaw members adapted to connect to an electrosurgical energy source to conduct energy through tissue grasped therebetween to effect a tissue seal; and a first linkage disposed at least partially within the shaft and operably coupled between the first jaw member and a second linkage by a coupling disposed proximal to the first linkage, wherein selective movement of the handle rotates the second linkage in a first direction, thereby rotating the first linkage in an opposite second direction to move the jaw members between the open and closed positions;

wherein a second end of the second linkage is operably coupled to a distal end of a drive element, the drive element operably coupled at a proximal end to the handle such that selective movement of the handle causes movement of the drive element relative to the shaft to cause rotational movement of the second linkage, and wherein the second end of the second linkage is configured to move within an aperture defined through the shaft upon selective movement of the handle, the aperture including a distal stop configured to limit rotational movement of the second linkage in the first direction and a proximal stop to limit rotational movement of the second linkage in a second direction.

9. An electrosurgical forceps, comprising:

a handle having a shaft extending therefrom and selectively movable to actuate a pair of first and second opposable jaw members pivotably connected to each other at a distal end of the shaft, the jaw members moveable from an open position, wherein the jaw members are in spaced relation relative to one another, to a closed position wherein the jaw members cooperate to grasp tissue therebetween, each of the jaw members adapted to connect to an electrosurgical energy source to conduct energy through tissue grasped therebetween to effect a tissue seal; and a first linkage disposed at least partially within the shaft and operably coupled between the first jaw member and a second linkage by a coupling disposed proximal to the first linkage, wherein selective movement of the handle rotates the second linkage in a first direction, thereby rotating the first linkage in an opposite second direction to move the jaw members between the open and closed positions;

wherein the coupling between the first linkage and the second linkage is movable between a first position to move the jaw members to the open position, and a second position to move the jaw members to the closed position in a releasably locked configuration, wherein the coupling between the first linkage and the first jaw member is collinear with the second end of the second linkage along a longitudinal axis, and wherein the first and second positions of the coupling between the first and second linkages correspond to opposite sides of the longitudinal axis.

10. An electrosurgical forceps, comprising:

a handle having a shaft extending therefrom and selectively movable to actuate a pair of first and second opposable jaw members pivotably connected to each other at a distal end of the shaft, the jaw members moveable from an open position, wherein the jaw members are in spaced relation relative to one another, to a closed position wherein the jaw members cooperate to grasp tissue therebetween, each of the jaw members adapted to connect to an electrosurgical energy source to conduct energy through tissue grasped therebetween to effect a tissue seal; and a first linkage disposed at least partially within the shaft and operably coupled between the first jaw member and a second linkage by a coupling disposed proximal to the first linkage, wherein selective movement of the handle rotates the second linkage in a first direction, thereby rotating the first linkage in an opposite second direction to move the jaw members between the open and closed positions;

wherein the first linkage is substantially linear and the second linkage is generally L-shaped.

11. A method of performing an electrosurgical procedure, the steps comprising:

providing an electrosurgical energy source;

providing an electrosurgical forceps, including:

a handle having a shaft extending therefrom and selectively movable to actuate a pair of first and second opposable jaw members pivotably connected to each other at a distal end of the shaft, the jaw members moveable from an open position, wherein the jaw members are in spaced relation relative to one another, to a closed position wherein the jaw members cooperate to grasp tissue therebetween, each of the jaw members adapted to connect to an the electrosurgical energy source to conduct energy through tissue grasped therebetween to effect a tissue seal; and a first linkage disposed at least partially within the shaft and operably coupled between the first jaw member and a second linkage disposed proximal to the first linkage;

selectively moving the handle to rotate the second linkage in a first direction, thereby rotating the first linkage in an opposite second direction to move the jaw members between the open and closed positions;

actuating the jaw members to grasp tissue therebetween;

rotating the first and second linkages into an over-the-center configuration to releasably lock the jaw members in the closed position; and delivering electrosurgical energy from the electrosurgical energy source to each of the jaw members to effect a tissue seal.

* * * * *